United States Patent [19]
Cross

[11] Patent Number: 5,243,712
[45] Date of Patent: Sep. 14, 1993

[54] DISPOSABLE URINARY DEVICE

[76] Inventor: Leta K. Cross, 169 Sage Rd., Houston, Tex. 77056

[21] Appl. No.: 527,582

[22] Filed: May 23, 1990

[51] Int. Cl.$^5$ .............................................. A47K 11/00
[52] U.S. Cl. ....................................... 4/144.2; 4/144.4
[58] Field of Search ............................ 4/144.2, 144.4; 141/337

[56] References Cited

U.S. PATENT DOCUMENTS

| | | | |
|---|---|---|---|
| 1,407,872 | 2/1922 | Lacy | 4/144.4 |
| 2,066,400 | 1/1937 | Hale | 4/144.3 X |
| 2,182,254 | 12/1939 | Farrell | 4/144.3 X |
| 2,690,568 | 10/1964 | Willis | 4/144.4 |
| 3,329,973 | 7/1967 | Bobbe | 4/144.2 |
| 3,597,770 | 8/1971 | Jacuzzi et al. | 4/144.2 |
| 3,613,122 | 10/1971 | Gross et al. | 4/144.4 |
| 4,023,216 | 5/1977 | Li | 4/144.3 |
| 4,305,161 | 12/1981 | Diaz | 4/144.2 |
| 4,528,703 | 7/1985 | Kraus | 4/144.2 |
| 4,531,245 | 7/1985 | Lowd et al. | 4/144.3 |
| 4,608,046 | 8/1986 | Towfigh | 4/144.3 X |
| 4,681,573 | 7/1987 | McGovern et al. | 4/144.3 X |
| 4,751,751 | 6/1988 | Reno | 4/144.4 |
| 4,815,151 | 3/1989 | Ball | 4/144.3 |
| 4,937,890 | 7/1990 | Tafur | 4/144.4 |

FOREIGN PATENT DOCUMENTS 2565956 12/1985 France .............................. 141/337

Primary Examiner—Henry J. Recla
Assistant Examiner—Robert M. Fetsuga
Attorney, Agent, or Firm—Gunn & Kuffner

[57] ABSTRACT

A disposable urinary device for use by females comprises a collapsible funnel-shaped body extending between an upper substantial rigid rim and a lower discharge opening. The body is provided with a pair of positioning loops for positioning the urinary device against the body of the user for directing urine away from the body of the user while urinating in an upright position.

7 Claims, 3 Drawing Sheets

DISPOSABLE URINARY DEVICE

BACKGROUND OF THE DISCLOSURE

This invention relates to urinary devices, particularly, to a disposable urinary device for use by a female to facilitate urination from a standing position.

Often times, females may find themselves in circumstances where urinating from a upright position is desirable and perhaps necessary. Many public facilities are unsanitary for use by females or may not be available. Females in today's society are also particularly conscious of contagious diseases which may be transmitted from contact with unsanitary toilet facilities. This is particularly true for facilities used by large numbers of individuals, for example, portable toilet facilities at a musical concert, sporting event or the like. The risk of contracting a contagious disease during such circumstances, particularly for a female who must normally contact the toilet seat to urinate, is perceived to be very high.

On occasion a female may be required to submit a urine specimen for medical testing or the like. This is often difficult for a female to accomplish without soiling her body or clothing. Urine specimens are normally collected in small bottles or containers which are usually not adapted for convenient use by a female in directing urine into the specimen container. For most females, it is awkward and difficult to gather a urine specimen in such a container without splashing urine on the body or clothing.

The desirability for a urinary device to aid a female to urinate from an upright position has been recognized in the prior art. Various devices, such as those disclosed in U.S. Pat. Nos. 3,329,973 (Bobbe), 4,608,046 (Towfigh), 4,681,573 (McGovern, et al.) and 4,751,751 (Reno) are representative of prior art attempts to provide a solution to a problem which is often encountered by females.

The cup-like device disclosed in U.S. Pat. No. 3,329,973 is open at the top end and closed at the bottom end. In use, the device is pressed directly against the body and positioned carefully to cover the opening of the urinary tract, the capacity of the device being adequate for a single use. In U.S. Pat. No. 4,608,046 the urinary aid includes an end which is insertable between the labia. Hand squeezing opens the insertable end of the urinary aid to form a urine receptive configuration which spread the labia as the device is pressed against the urinary meatus.

In U.S. Pat. No. 4,681,573 the urinary device comprises a flat blank which may be folded to form a conical-like urinary device. The device must be properly positioned and carefully held to cover the opening of the urinary tract during use. In U.S. Pat. No. 4,751,751 the funnel like urinary device includes an upper end which is curved to envelope the exterior of the female vaginal area and a lower end portion formed into a spout-like shape.

Thus, while attempts have been made in the past to provide urine collecting or directing devices for female use, in general these devices have required a learning process and skill in handling for proper usage. These devices are bulky and in some instances require the user to assemble the funnel-like device from a flat blank which if not properly erected will tend to leak and will not achieve the desired result. Some of these devices have been designed for reuse. These reusable devices must therefore be cleaned after each use and stored in a handbag or the like for subsequent use. Such devices are awkward, unsanitary and inconvenient to use, particularly after initial use whereupon cleaning the device is required.

It is therefore a primary object of the present invention to provide a disposable urinary device for use by females which is compact and convenient to use. The urinary device of the present invention requires no assembly and is easily properly positioned and secured for use with two fingers.

SUMMARY OF THE INVENTION

The present invention is directed to a disposable urinary device for use by a female to facilitate urination from an upright position. The urinary device is in the form of a cone or funnel. The funnel portion of the device is pleated so that in the storage configuration the funnel is collapsed onto itself to present a substantially flat, compact profile. The urinary device of the invention contemplates one hand operation accomplished by inserting two fingers into a pair of loops positioned adjacent to the upper opening of the device. The upper opening of the urinary device is substantially oval in shape and dimensioned to envelop the exterior of the female vaginal area when pressed against the body by the user with two fingers inserted through the placement loops. The lower end of the urinary device is formed in a spout-like shape for directing urine away from the user's body.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrated only typical embodiments of this invention and are therefore not to be considered limiting of its scope, for the invention may admit to other equally effective embodiments.

DETAILED DESCRIPTION OF THE PREFERRED EMBODIMENT

Figure 1:
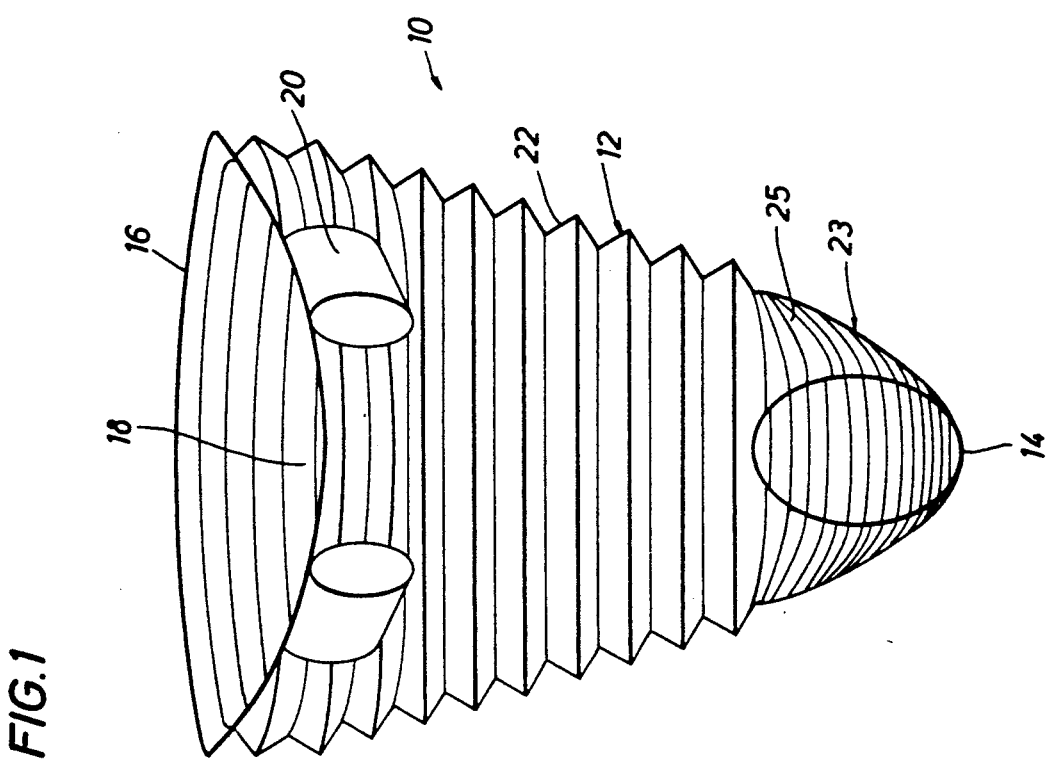
FIG. 1 is a front, elevational view of the urinary device of the invention.

Referring first to FIG. 1, the urinary device of the present disclosure is generally identified by the referenced numeral 10. The urinary device 10 is formed of a paper-like material which is completely disposable. The material of the device 10 is biodegradable and flushable. Upon contact with water for a short period of time, the device 10 becomes pliant and easily flushes down a toilet without clogging the plumbing or otherwise hampering the disposal of waste through the toilet facilites.

The urinary device 10 of the present disclosure comprises a funnel-like body 12 open at each end and defining an axial passage extending between the open ends. The body 12 tapers downwardly and terminates at an outlet end. The upper end of the body 12 is open and defined by an upper edge 16. The upper edge 16 circumscribes an opening 18 which is substantially oval in shape conforming approximately to the contour of the female body which the opening 18 will circumscribe when the device 10 is in use.

In the preferred embodiment of the invention, the upper edge or rim 16 is outwardly rolled to form the substantially rigid rim 16. The rim 16 however may be formed in some other fashion provided that sufficient rigidity is maintained for forming and maintaining the substantially oval opening 18. While the rim 16 is sufficiently rigid to maintain the oval opening 18, the rim 16 is sufficiently pliant so that it may be squeezed together or spread to accommodate variations in dimensions of the female anatomy.

A pair of placement or positioning loops 20 are located on opposite sides of the rim 16 for holding the device 10 in proper position against the body when urinating. The loops 20 are adapted to receive the index and middle finger of a user and are positioned slightly off center toward the front of the device 10 as best shown in FIG. 1. The fingers of a user are inserted into the loops 20 and are spread to form a "V". With fingers spread, the user presses the rim 16 against the body thereby holding the urinary device 10 in a proper position for urination. The loops 20 are glued or otherwise attached to the rim 16.

Figure 3:
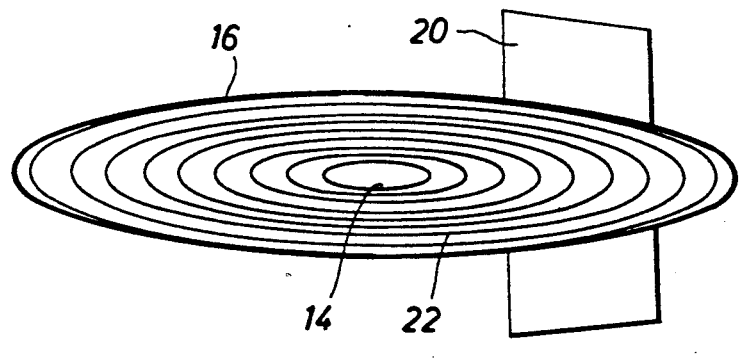
FIG. 3 is a top plan view of the urinary device of the invention shown in its collapsed position.
Figure 4:
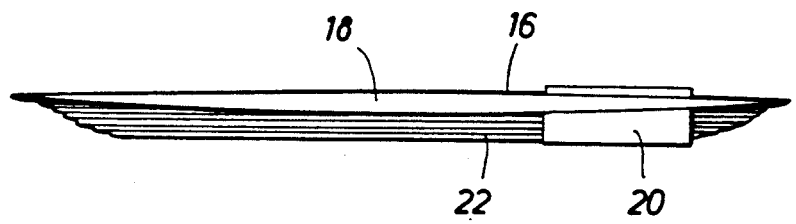
FIG. 4 is a side view of the urinary device of the invention shown in its collapsed position.

The body 12 of the urinary device 10 is horizontally pleated thereby presenting an accordion-like profile. The pleats 22 and 25 permit the body 12 to be collapsed onto itself to form a substantially flat, compact profile as shown in FIGS. 3 and 4. The flat profile is particularly desirable for individually packaging the urinary device 10 so that one or more may be conveniently carried in a typical handbag or the like. The flat profile of the urinary device 10 also lends itself to use with coin operated dispenser machines which may be located in public toilet facilities where the need for the urinary device 10 is the greatest. The urinary device 10 may thus be easily dispensed from a machine, used and discarded.

Referring again to FIGS. 1 and 2, the pleated body 12 of the urinary device 10 tapers downwardly toward the discharge or outlet end 14. The pleats 22 and 25 decrease in diameter along the longitudinal length of the body 12 toward the outlet end 14. This permits the pleats 22 and 25 of the body 12 to collapse inwardly toward the longitudinal axis of the body 12, thereby forming a substantially flat profile having a maximum diameter defined by the rim 16 as shown in FIG. 4.

Figure 2:
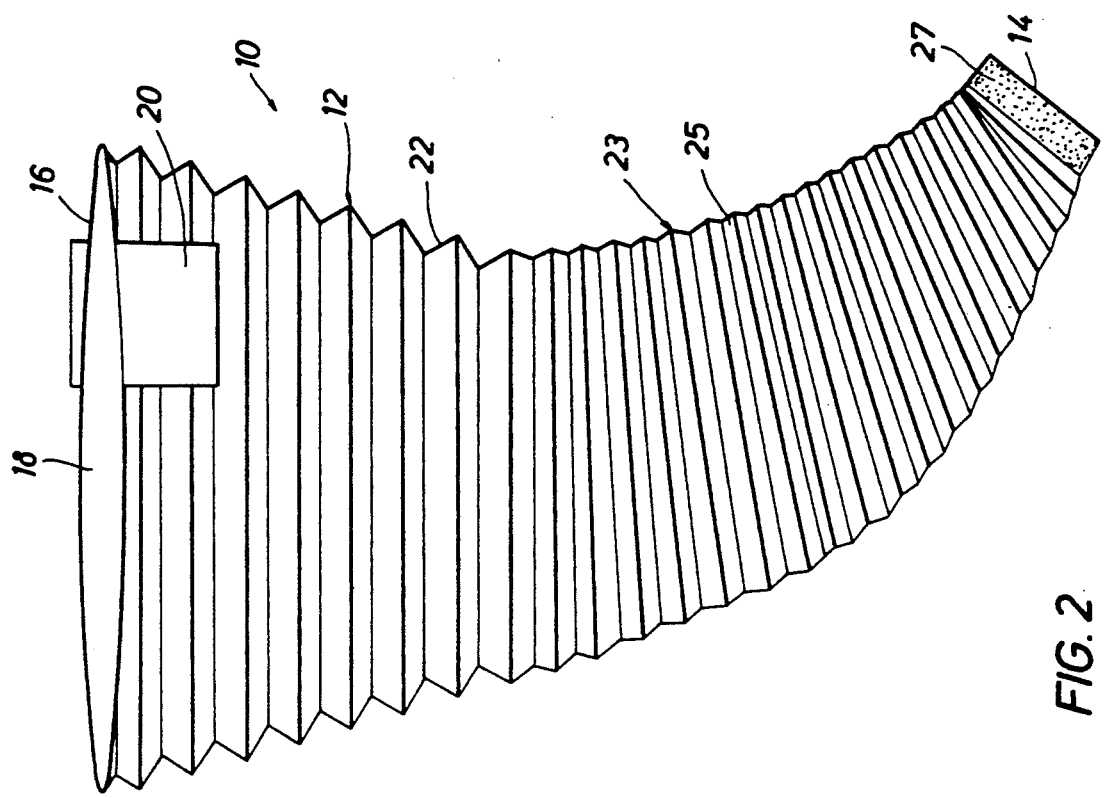
FIG. 2 is a side, elevational view of the urinary device of the invention.

The lower portion of the body 12 forms a spout 23 terminating at the outlet end 14. The spout 23 extends angularly outwardly toward the front of the body 12, i.e., toward the right in FIG. 2, for directing urine forwardly away from the body of a female using the urinary device 10. The pleats 25 defining the spout 23 are gathered closer together along the front of the spout portion of the body 12 than the back of the body 12 so that the spout 23, when fully extended, is angularly directed relative to the longitudinal axis of the body 12, as best shown in FIG. 2. The spout 23, as shown in FIG. 2 for illustrative purposes, is relatively short for use by a female to urinate while standing. It is understood however that the spout 23 may be formed so that when it is extended it is sufficiently long for use by a female confined to a wheelchair or the like.

In use, the urinary device 10 is stretched outwardly from the rim 16 by the user to form the funnel-shaped body 12 as shown in FIGS. 1 and 2. The index and middle finger of the user are inserted in the loops 20 and the device 10 is pressed directly against the female body for urination while standing. In this manner, urine is directed away from the user's body and the user avoids coming into physical contact with the toilet facilities. After use, the urinary device 10 is discarded into the toilet bowl and flushed away.

In the preferred embodiment, the urinary device 10 is formed of a paper-like material which is flushable and biodegradable. The interior surface of the funnel like body 12 is coated with a water proof or water resistant material. The exterior surface of the body 12 is water absorbant and may be used as a self-wipe if desired. The external surface of the body 12 may also be impregnated with a deodorant or other feminine hygienic composition. The end 14 of the spout 23 is outwardly folded or rolled so that a strip 27 of fluid resistant material externally surrounds the outlet end 14. The rolled rim 16 is also coated with fluid resistant material. The external strip 27 and rim 16 form fluid resistant barriers so that urine directed through the device 10 and exiting the end 14 does not contact the external absorbant surface of the body 12.

Figure 5:
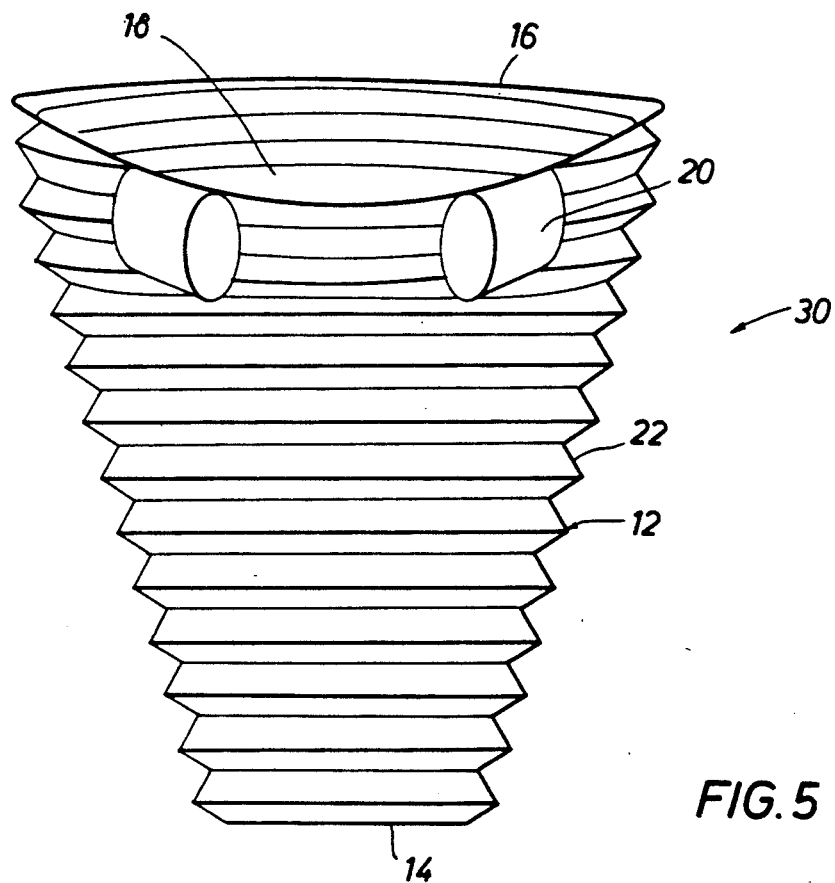
FIG. 5 is a front, elevational view of an alternate embodiment of the urinary device of the invention.

In the preferred embodiment, the urinary device 10 of the invention is collapsible, disposable and biodegradable. It is understood however that the urinary device 10 may also be formed of other materials which are non-collapsible and non-disposable. The body 12 of the urinary device 10 may be a straight funnel as shown in the alternate embodiment of FIG. 5. The device 30 of FIG. 5 is substantially identical to the preferred embodiment shown in FIG. 1, therefore like reference numerals have been used to identify like components. The device 30 does not include the angularly directed spout 23 shown in FIG. 1. The fluid passage between the opening 18 outlet 14 defines a substantially straight conical cavity. The device 30 is used in the same manner as the device 10, requiring only that the user stand more directly above the toilet opening when using the urinary device 30

While the foregoing is directed to the preferred embodiment of the present invention, other and further embodiments of the invention may be devised without departing from the basic scope thereof, and the scope thereof is determined by the claims which follow.

What is claimed is:

1. A urinary device for female use, comprising:
   a) a downwardly tapering, collapsible, funnel-shaped, one piece unitary body defining an axial passage extending therethrough;
   b) a substantially rigid rim defining an upper end of said body, said rim circumscribing a substantially oval shaped opening forming said upper end of said body;
   c) a discharge opening defining a lower end of said body, said discharge opening being in fluid communication with said oval opening, said discharge opening and said oval opening defining opposite ends of said axial passage extending therebetween;
   d) a pair of positioning loops secured opposite each other on said body adjacent said rim for positioning said funnel-shaped body to generally circumscribe a female urinary tract for directing urine away fronm the female body;

e) wherein said funnel-shaped body is defined by a plurality of pleats progressively decreasing in diameter from said rim to said discharge opening, and wherein each of said pleats define a horizontal plane substantially perpendicular to said axial passage of said funnel-shaped body;

(f) an outwardly extendible spout formed by said plurality of pleats defining the lower end of said body, said pleats being gathered along a longitudinal front portion of said funnel-shaped body for positioning said spout at an angle relative to the longitudinal axis of said funnel-shaped body upon extending said funnel-shaped body for use; and g) wherein said funnel-shaped body is inwardly collapsible onto itself along its longitudinal axis for forming a substantially flat storage profile.

2. The apparatus of claim 1 wherein said pair of loops are offset toward a forward portion of said body and are adapted to receive fingers of the user therein.

3. The apparatus of claim 1 wherein said body is internally coated with a water resistant composition and the external surface of said body is sufficiently pliant for use as a self-wipe.

4. The apparatus of claim 3 wherein the external surface of said body is impregnated with a feminine hygiene composition.

5. The apparatus of claim 1 wherein said rim defines the maximum diameter of said funnel-shaped body.

6. The apparatus of claim 1 wherein said spout includes an external fluid resistant strip about said discharge opening at the lower end of said body.

7. A urinary device for female use, comprising:

a) a downwardly tapering, collapsible, funnel-shaped body defining an axial passage extending therethrough;

b) a substantially rigid rim defining an upper end of said body, said rim circumscribing a substantially oval shaped opening forming said upper end of said funnel-shaped body;

c) a discharge opening defining a lower end of said funnel-shaped body, said discharge opening being in fluid communication with said oval opening, said discharge opening and said oval opening defining opposite ends of said axial passage extending therebetween;

d) an outwardly extending spout forming the lower end of said funnel-shaped body;

e) wherein said funnel-shaped body is defined by a plurality of pleats progressively decreasing in diameter from said rim to said discharge opening, and wherein said pleats defining said spout are gathered along a front portion of said funnel-shaped body permitting said spout to extend outwardly at an angle relative to the longitudinal axis of said funnel-shaped body;

f) positioning means secured adjacent to said rim for positioning said funnel-shaped body to generally circumscribe a female urinary tract for directing urine away from the female body; and (g) wherein said funnel-shaped body includes an external fluid resistant strip located about said discharge opening for forming a fluid barrier between said discharge end and the external surface of said funnel-shaped body.

* * * * *